(12) United States Patent
Lin et al.

(10) Patent No.: US 7,760,930 B2
(45) Date of Patent: Jul. 20, 2010

(54) TRANSLATION ENGINE OF DEFECT PATTERN RECOGNITION

(75) Inventors: Chen-Ting Lin, Hsinchu (TW);
Chih-Cheng Chou, Hsinchu (TW);
Chih-Hung Wu, Taipei (TW);
Chia-Hua Chang, Sindian (TW)

(73) Assignee: Taiwan Semiconductor Manufacturing Company, Ltd., Hsin-Chu (TW)

(*) Notice: Subject to any disclaimer, the term of this patent is extended or adjusted under 35 U.S.C. 154(b) by 1006 days.

(21) Appl. No.: 11/358,664

(22) Filed: Feb. 21, 2006

(65) Prior Publication Data
US 2007/0196012 A1    Aug. 23, 2007

(51) Int. Cl.
*G06K 9/00* (2006.01)

(52) U.S. Cl. ........................ 382/149; 382/141; 382/142; 382/143; 382/144; 382/145; 382/146; 382/147; 382/148; 382/150; 382/151; 382/152; 382/181; 348/86; 348/87; 348/88; 348/89; 348/90; 348/91; 348/92; 348/93; 348/94; 348/95; 348/125; 348/126; 348/127; 348/128; 348/129; 348/130; 348/131; 348/132; 348/133; 348/134; 438/16

(58) Field of Classification Search ......... 382/141–152, 382/181; 438/16; 348/86–95, 125–134
See application file for complete search history.

(56) References Cited

U.S. PATENT DOCUMENTS

| | | | |
|---|---|---|---|
| 4,809,308 A * | 2/1989 | Adams et al. | 382/150 |
| 5,960,106 A | 9/1999 | Tsuchiya et al. | |
| 7,106,897 B1 * | 9/2006 | McIntyre et al. | 382/145 |
| 2002/0181756 A1 * | 12/2002 | Shibuya et al. | 382/145 |
| 2003/0072481 A1 * | 4/2003 | Wooten et al. | 382/145 |

FOREIGN PATENT DOCUMENTS

| | | |
|---|---|---|
| CN | 1384467 A2 | 12/2002 |
| JP | 63156288 | 6/1988 |
| JP | 2004251781 | 9/2004 |
| TW | 226591 B | 1/2005 |

OTHER PUBLICATIONS

Chinese Patent and Trademark Office, Chinese Office Action dated Jun. 27, 2008, Application No. 200610107809X, 7 pages.

* cited by examiner

*Primary Examiner*—Vikkram Bali
*Assistant Examiner*—Daniel Zeilberger
(74) *Attorney, Agent, or Firm*—Haynes and Boone, LLP

(57) ABSTRACT

The present disclosure provides a system and method for recognizing a defect image associated with a semiconductor substrate. In one example, the method includes collecting defect data of the defect image by testing and measuring the semiconductor substrate, extracting a pattern from the defect data, normalizing a location, orientation, and size of the pattern, and identifying the pattern after the pattern is normalized.

20 Claims, 9 Drawing Sheets

TRANSLATION ENGINE OF DEFECT PATTERN RECOGNITION

BACKGROUND

Semiconductor integrated circuits wafers, each comprising multiple chips, are produced by a plurality of processes in a wafer fabrication facility (fab). Each process step can introduce new defects, quality and reliability issues, failures, and yield losses. To improve manufacturing technologies and enhance chip (wafer) quality, reliability, and yield, the semiconductor wafers are measured, tested, monitored, and analyzed using a method such as failure mode analysis. The analysis includes a defect pattern recognition. However, current practices using defect pattern recognition rely on the creation of complex recognition rules or complicated models, resulting in low efficiency and effectiveness.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figures 1A, 1B:
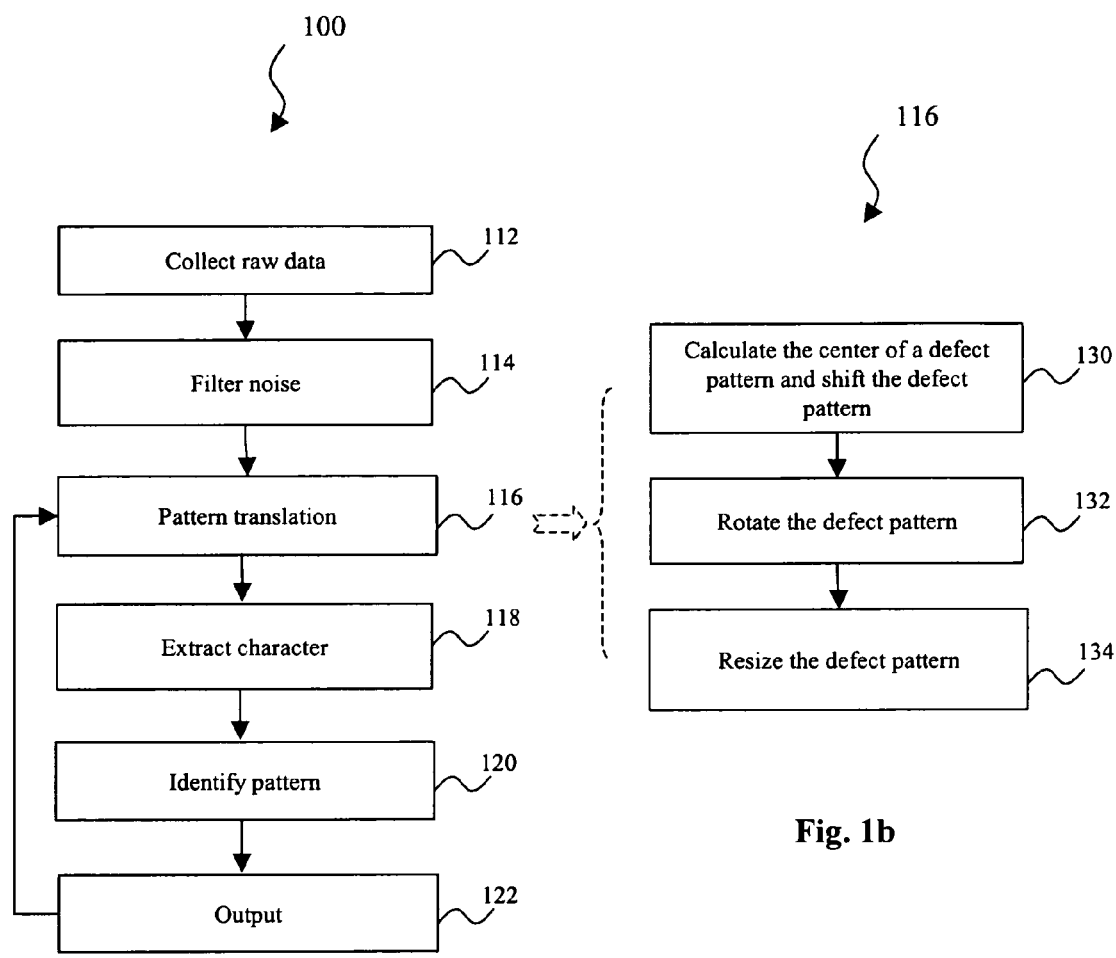
FIG. 1a is simplified flowchart of one embodiment of a method for implementing defect pattern recognition.
FIG. 1b is a simplified flowchart of one embodiment of a method for normalizing a defect pattern.

It is to be understood that the following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

FIG. 1a is a simplified flowchart of one embodiment of a method 100 for recognizing a defect pattern formed on a substrate processed in a semiconductor fabrication facility (fab). The method 100 begins at step 112 by collecting raw data of a defect image on the substrate. The substrate may be a semiconductor wafer (wafer), a photomask (mask), or other substrates such as a thin-film-transistor liquid crystal display (TFT-LCD) substrate processed in a semiconductor fabrication (fab). Taking a wafer as an example, the wafer may go through a plurality of processes in a semiconductor fab that form multiple chips on the wafer, each chip comprising a functional integrated circuit. Each process step may introduce new defects to the wafer, including physical defects, electrical defects, and other types of defects. The physical defects may include scratches, contaminations, and particles, chipping, and cracks. The electrical defects may include shorts, open lines, and out of specification electrical parameters (such as sheet resistance). These defects may be inspected for and measured by metrology tools such as inspection tools and/or probe test tools. Defects of one type distributed on a wafer may be extracted to form a defect image that may include one or more defect patterns. A defect pattern may be associated with a certain failure mechanism. Recognition of a defect pattern may aid in failure mode analysis and lead to root cause(s) identification.

Figure 2:
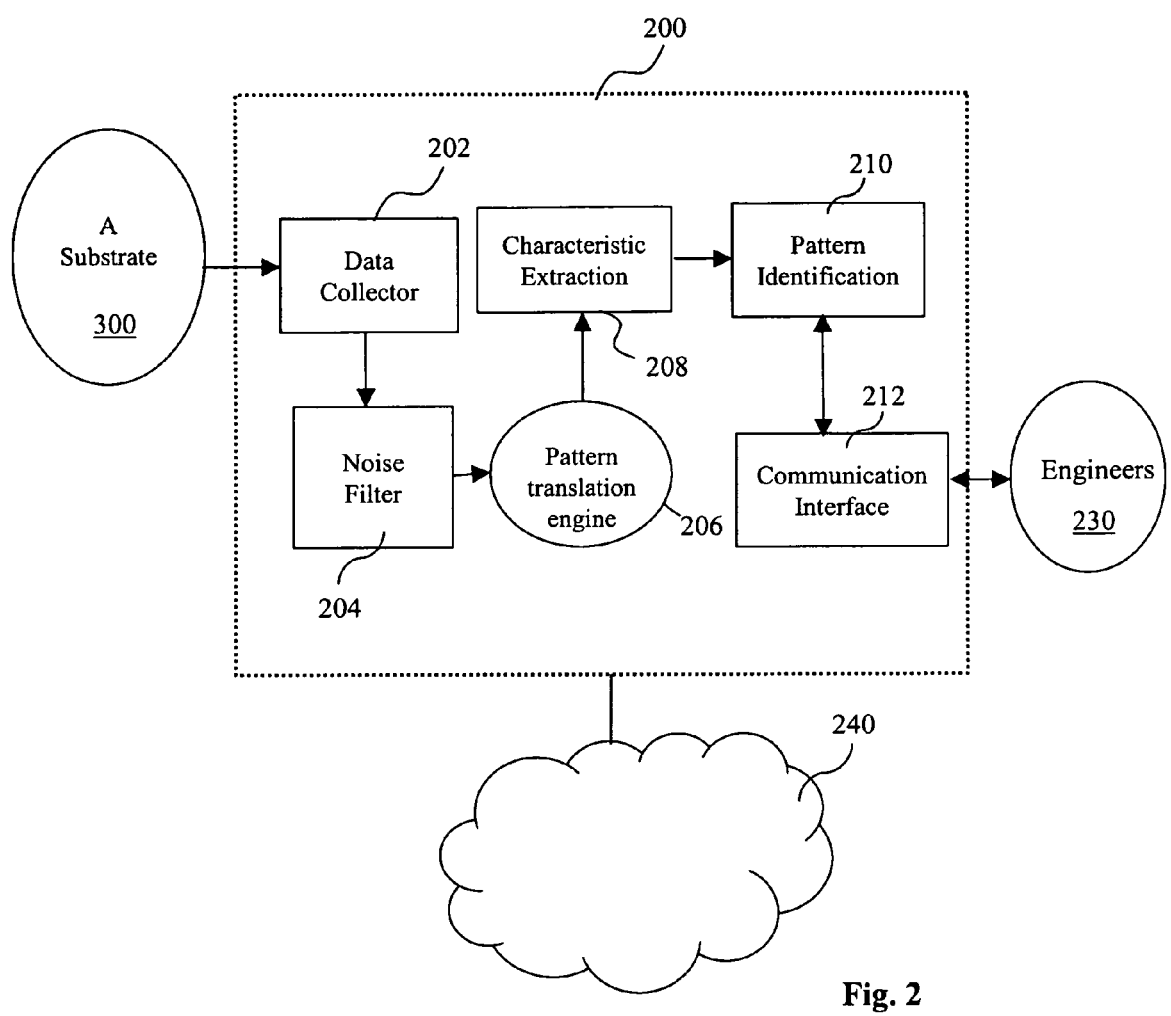
FIG. 2 is a block diagram of one embodiment of a pattern translation engine that may be used to implement the method of FIG. 1a and the method of FIG. 1b.

With additional reference to FIG. 2, the metrology tools used to extract defect data may involve electrical, optical, and analytical tools such as microscopes, micro-analytical tools, line width measurement tools, mask and reticle defect tools, particle distribution tools, surface analysis tools, stress analysis tools, resistivity and contact resistance measurement tools, mobility and carrier concentration measurement tools, junction depth measurement tools, film thickness measurement tools, gate oxide integrity test tools, C-V measurement tools, focused ion beam (FIB), and other test and measurement tools.

Figure 3A:
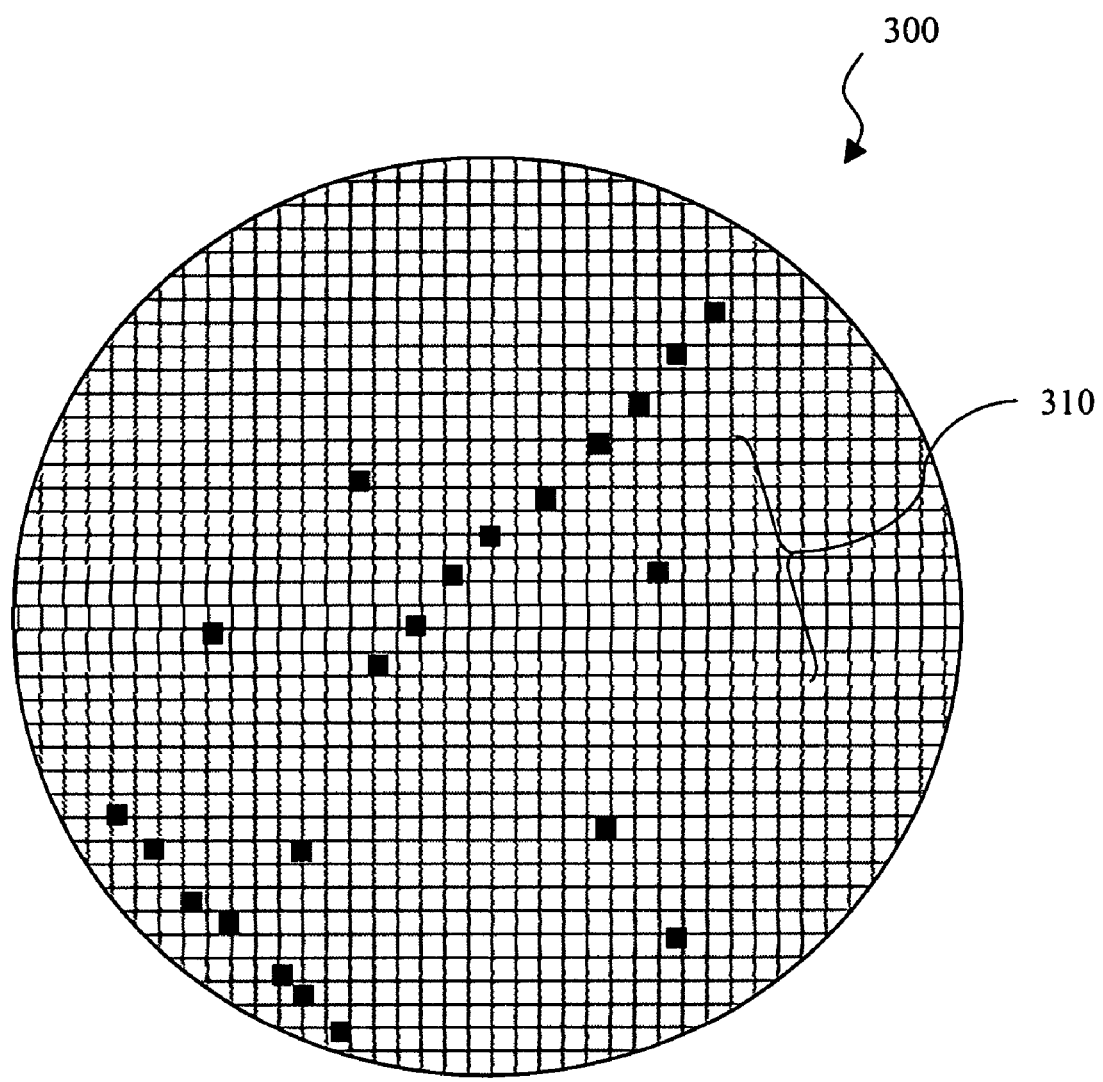
FIGS. 3a through 3f are schematic views of one embodiment of a substrate having defects during various stages of defect pattern recognition.

After inspections, measurements, and/or tests, an image of defects on a wafer may be collected from at least one of the metrology tools. A data collector 202 in the defect pattern recognition system 200 of FIG. 2 may be implemented to collect defect data. The data collector 202 may comprise both hardware and software in extracting and storing defect data from the metrology tools. The hardware of the data collector may include or connect to various metrology tools. An exemplary semiconductor substrate 300, having defects of a type formed thereon, is illustrated in FIG. 3a, wherein the defects of a particular type form a defect image 310.

Figure 3B:
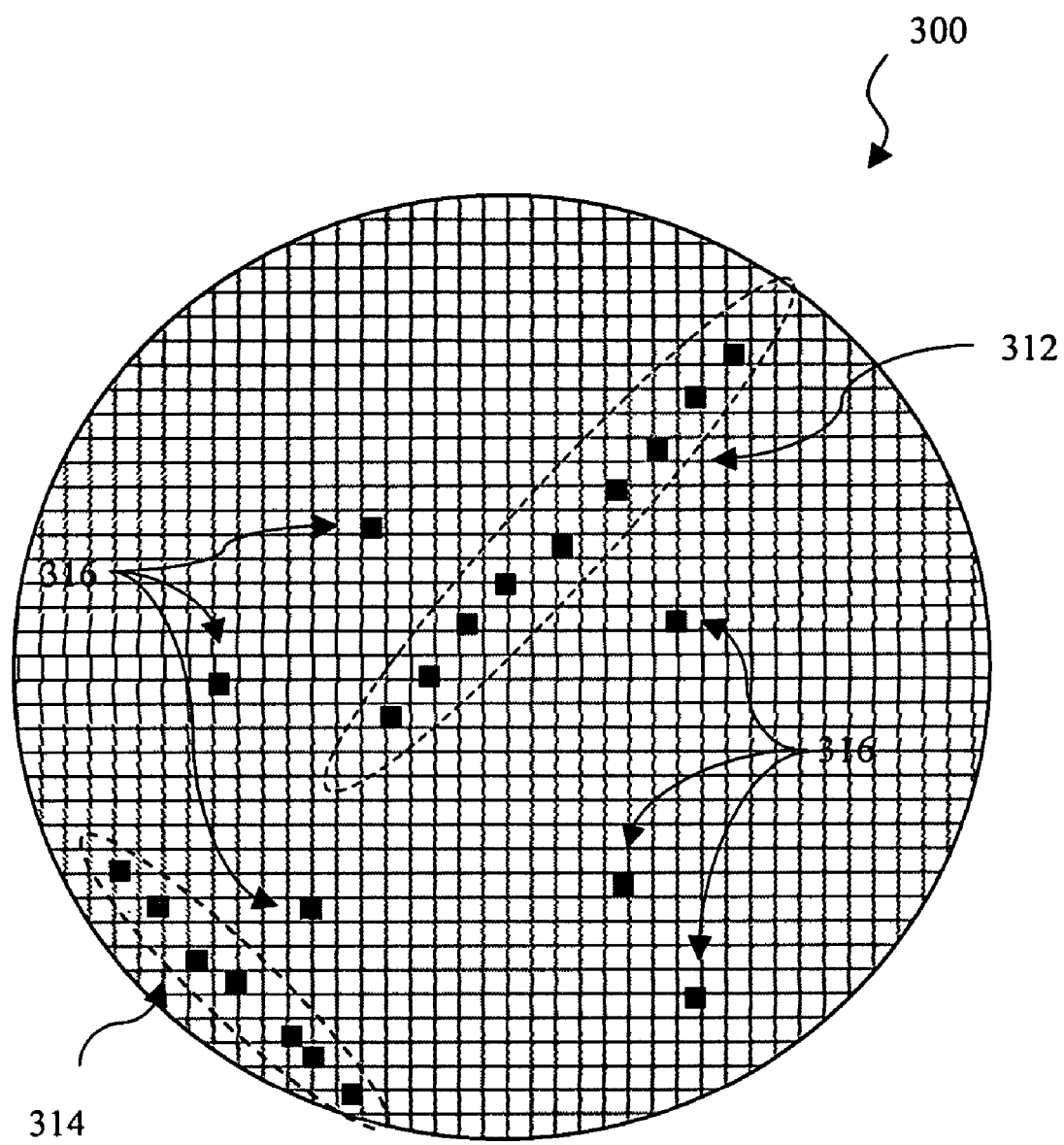
Figure 3C:
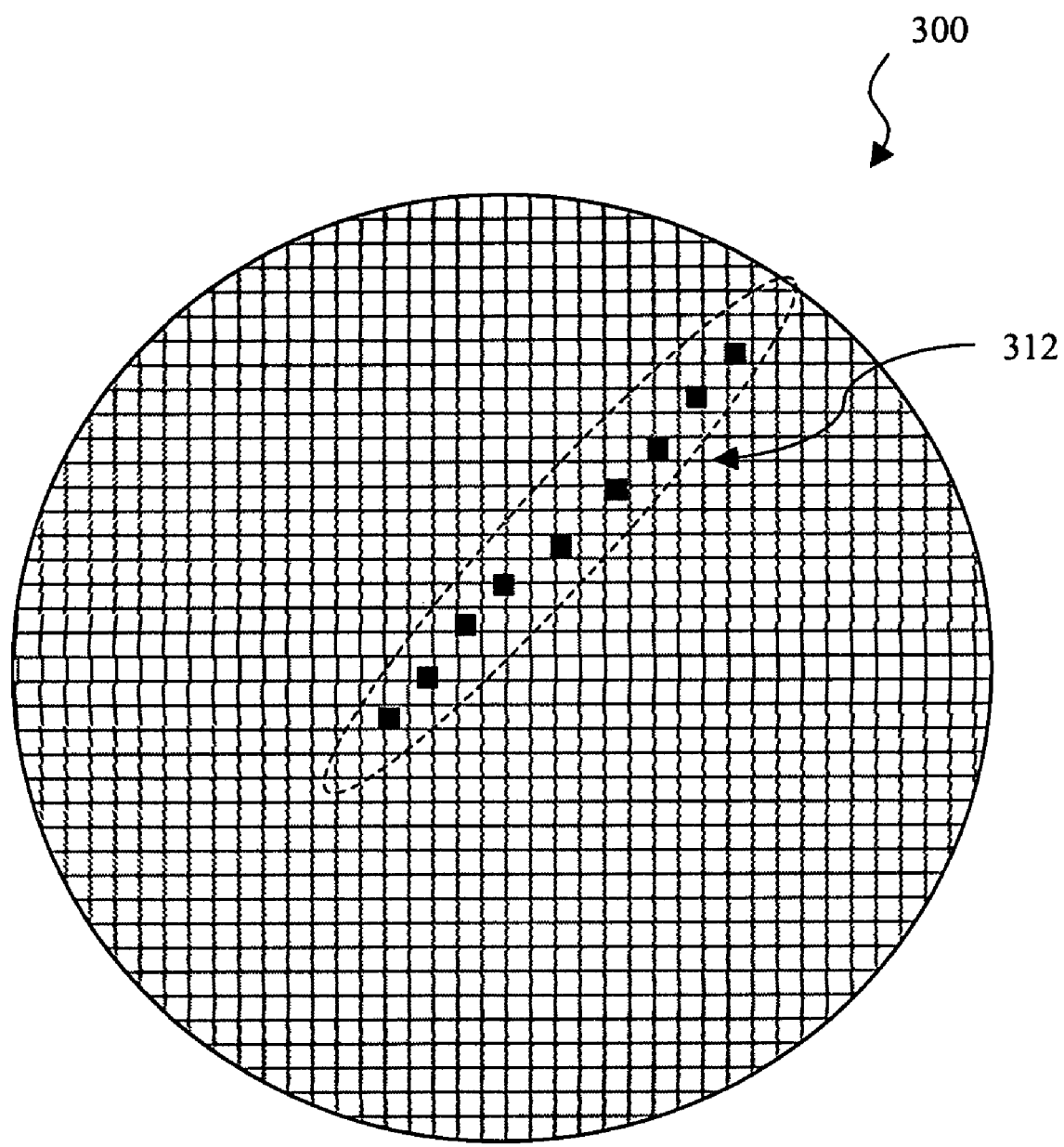

The method 100 proceeds to step 114 to filter the defect image to eliminate noise, which may be performed by a noise filter module 204 of the defect pattern recognition system 200. In one embodiment, defect clusters having a low density below a predefined criteria, such as scattered defects 316 (FIG. 3b), may be treated as noise and eliminated from the defect image. Then, the defect image may be further evaluated to separate one or more defect patterns therefrom, such as exemplary defect patterns 312 and 314 (circled for clarity in FIG. 3b). It is understood that defect patterns may have different dimensions, different locations, different orientations, and different geometrical shapes (e.g., lines, curves, a set of rays, rings, and half-rings). The exemplary defect patterns 312 and 314 appear as defect lines. The separated patterns may be labeled and one of them may be selected each time for pattern translation and identification, then the next one is selected to repeat the same process until all labeled patterns are exhausted. The defect pattern 312 is selected and isolated, shown in FIG. 3c, as an example to describe the following pattern analysis processes.

The method 100 proceeds to step 116 to perform a pattern translation process to normalize patterns in location, orientation, and dimension. The pattern translation may be utilized by a pattern translation engine 206 of the defect pattern recognition system 200. A more detailed example of the pattern translation process of step 116 is described with respect to FIG. 1b.

Figure 3D:
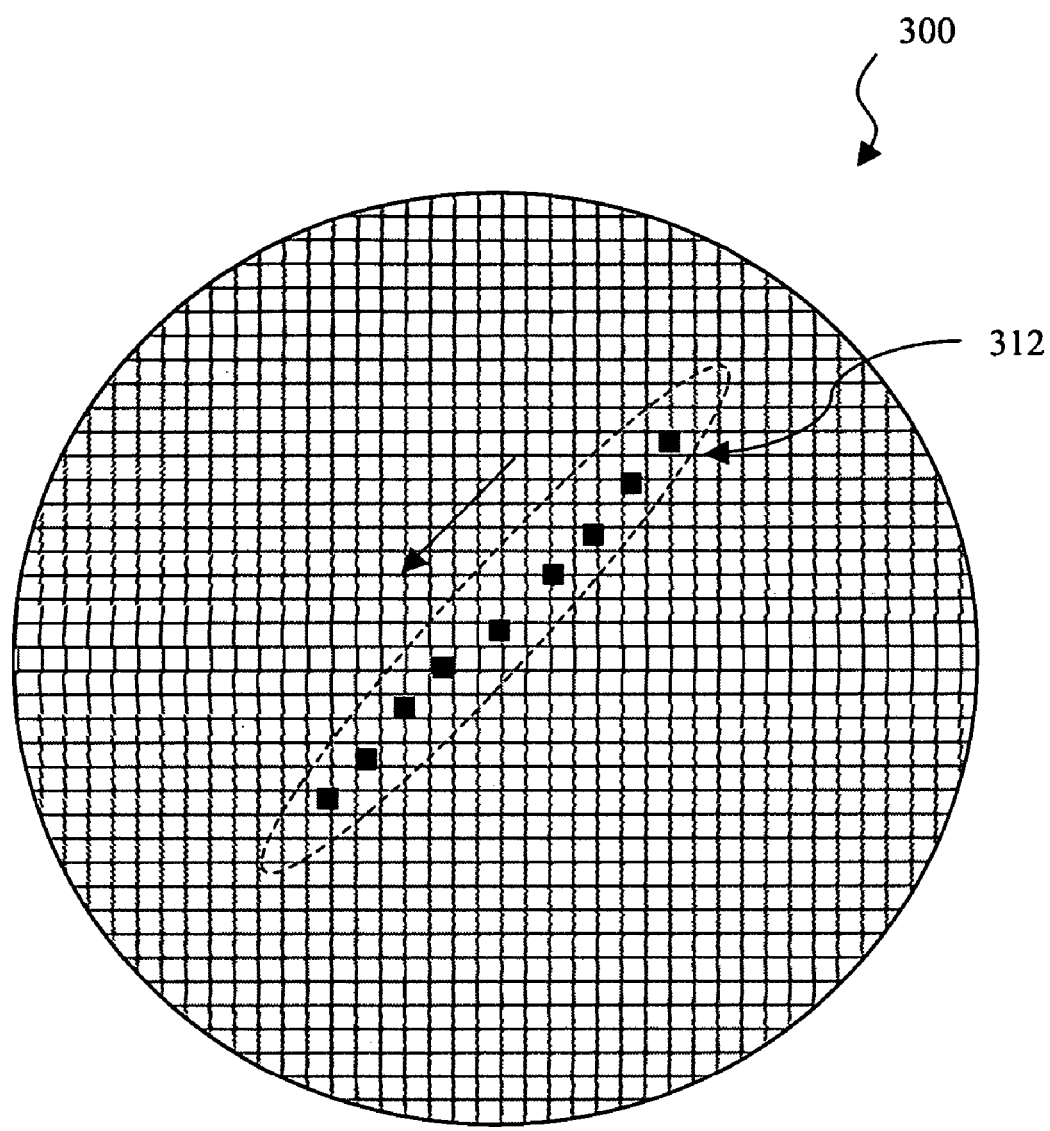
Figure 3E:
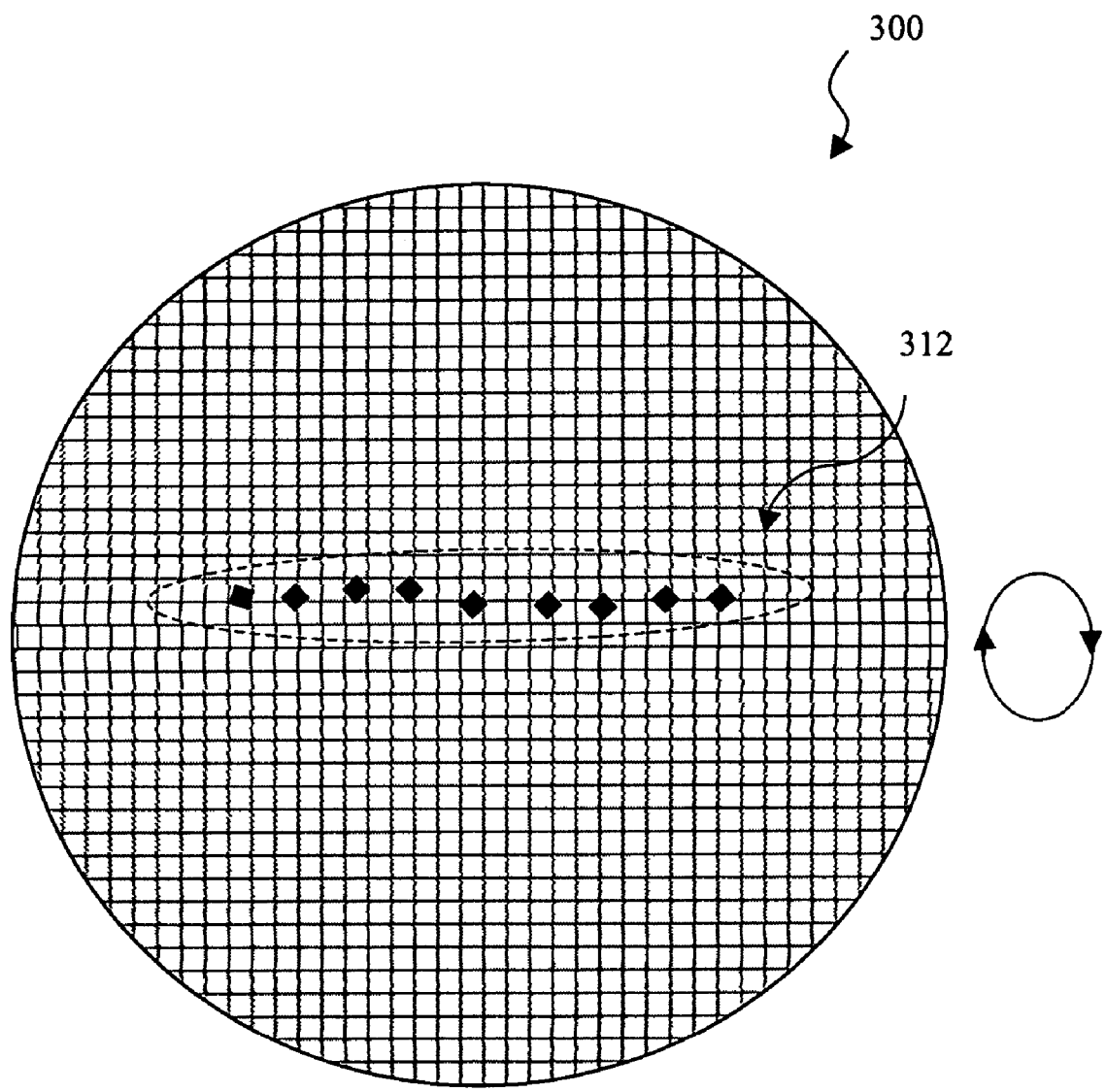
Figure 3F:
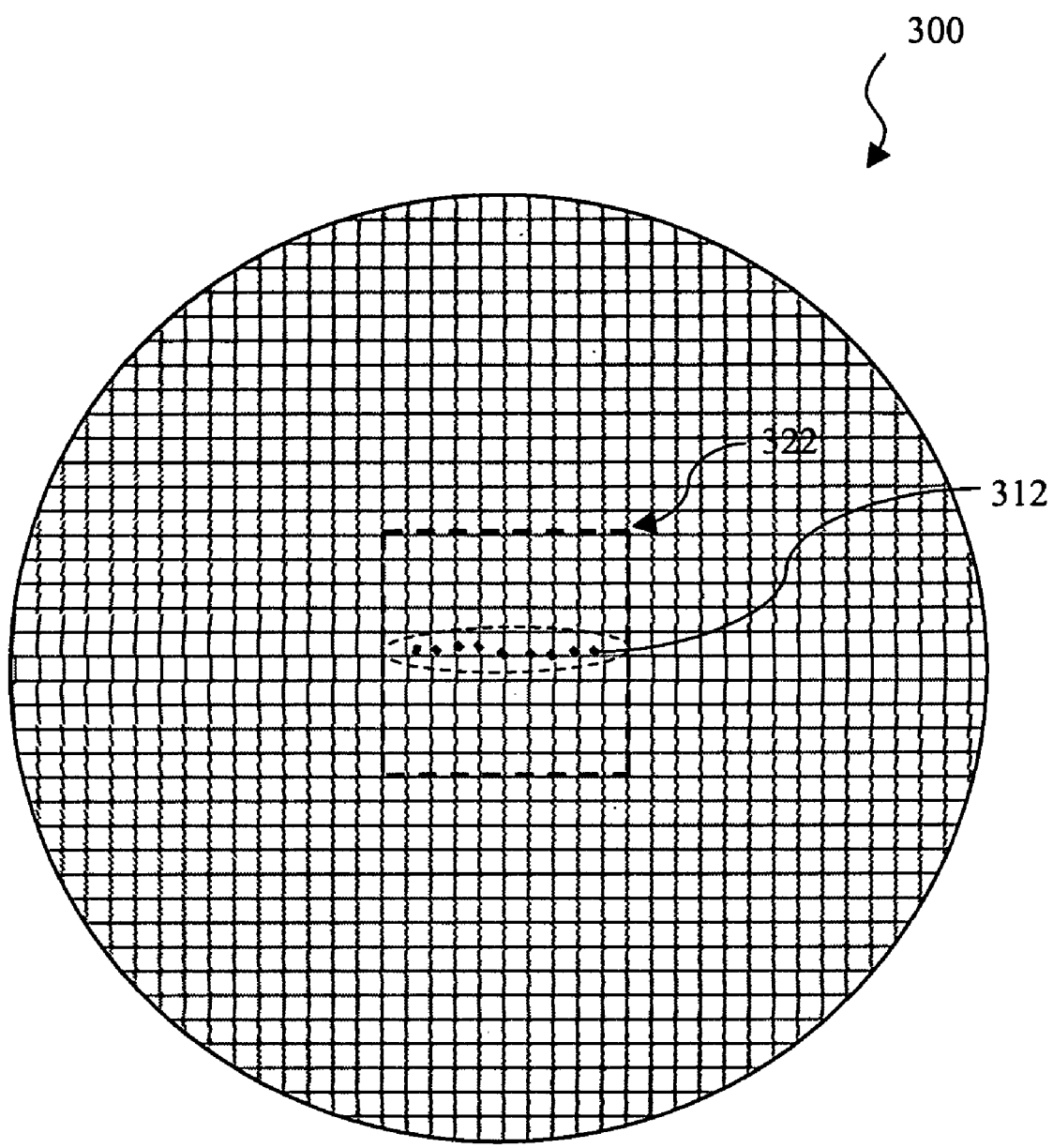

Referring to FIG. 1b, the pattern translation process of step 116 includes a sub-step 130 to calculate the center of the defect pattern and shift the defect pattern such that the center of the defect pattern is set at an origin. For example, the defect pattern 312 may be shifted as illustrated in FIG. 3d. The defect pattern may not be associated with the substrate as long as it is isolated. The center of the defect pattern may be defined as the average of the positions of all defects in the defect pattern, with each position weighted equally or as defined otherwise. The pattern translation process 116 continues to sub-step 132 to rotate the defect pattern such that a specific direction of the defect pattern is oriented. For example, the defect pattern 312 may be rotated as illustrated in FIG. 3e. The special direction may be defined as a line connecting two defects that are separated by the greatest distance within the defect pattern. The defect pattern may be rotated clockwise such that the special direction may be horizontally oriented. The pattern translation process 116 then continues to sub-step 134 to resize the defect pattern such that the defect pattern is just within predefined limits (or a predefined area). For example, the defect pattern 312 may be resized (e.g., expanded or shrunk in scale in both perpendicular directions) to be just within a predefined square 322 as illustrated in FIG. 3f. Thus, a normalized defect pattern is provided for later steps of the method 100 for further pattern processing. It is understood that the normalization sub-steps may not be implemented in the above order.

The method 100 proceeds to step 118 to extract one or more characteristics from the normalized defect pattern, which may be accomplished by a characteristic extraction module 208 of the defect pattern recognition system 200. The characteristic extraction process may extract pattern parameters such as average pattern density, core pattern density, edge pattern density, width/length ratio, relative area (defined as an area of the normalized defect pattern relative to the area of the predefined limits such as the square 322, and area/perimeter ratio. The extracted parameters may be used in defect pattern recognition as described with respect to step 120.

The method 100 proceeds to step 120 to identify the defect pattern based on the normalized defect pattern and/or extracted parameters therefrom. The pattern identification process may be utilized by a pattern identification module 210 of the defect pattern recognition system 200 and may be further supported by a database comprising a plurality of standard defect patterns and/or a plurality of defect pattern rules. The defect pattern identification may be model-based, rule-based, or combination of both. In one example, the normalized defect pattern is compared with each of the standard defect patterns stored in the database until one standard defect pattern is accepted according to predefined criteria. The comparison may be based on a formula such as a summation of a discrepancy function over all points within the predefined limits. In another example, the extracted parameters may be incorporated into a formula to evaluate and identify the pattern. In another example, each of the plurality of defect pattern rules may be used to judge the extracted parameters of the defect pattern until the defect pattern is identified to be one of the standard defect patterns or all of the defect pattern rules are rejected. In a further example, two or more of the above described methods are combined to identify the defect pattern.

The result produced by step 120 of the defect pattern identification process may be provided to users such as engineers 230, who may obtain the results through a communication interface 212 of the defect pattern recognition system 200.

The method 100 may then return to step 116 to repeat the processing for another labeled defect pattern (such as 314 of FIG. 3b) until all of the labeled defect patterns are exhausted.

The defect pattern recognition system 200 may comprise both software and hardware and may be connected to a local network 240 and further connected to a virtual fab or a part of the virtual fab (described in more detail later). Each functional module and the various functions of the system 200 may be configured and coordinated to implement the defect pattern recognition.

Since the defect patterns are normalized, the defect pattern recognition may be simplified and designed more efficiently. For example, similar defect patterns with different locations, orientations, and dimensions are now normalized and may be treated as the same defect pattern. For instance, the defect patterns 312 and 314 may both be identified as a line-type defect pattern. The number of rules and formulas needed to deal with defect pattern differences of location, orientation, and dimension may be reduced or eliminated.

Figure 4:
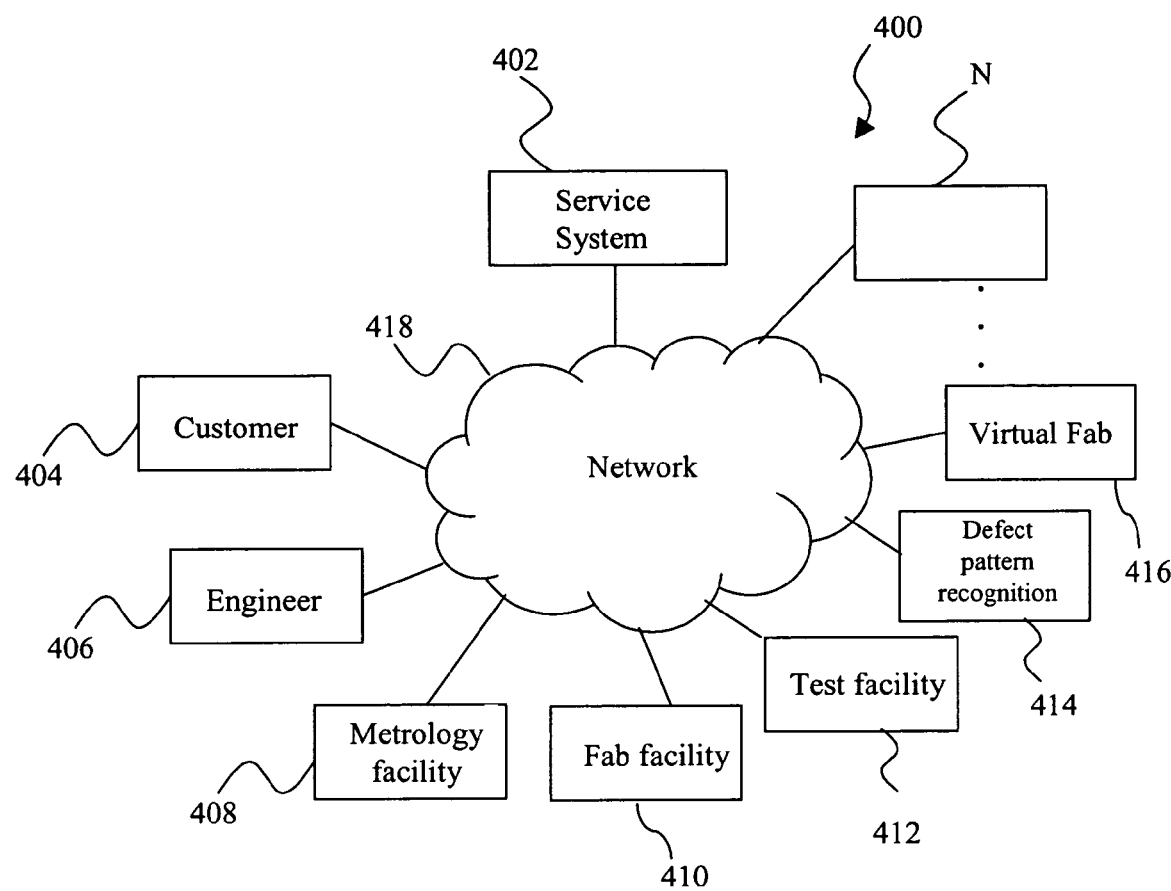
FIG. 4 is a block diagram of one embodiment of a virtual fabrication system within which the translation engine of FIG. 2 may be utilized.

Referring now to FIG. 4, a virtual IC fabrication system (a "virtual fab") 400, to which the defect pattern recognition system 300 of FIG. 3 may be connected, is illustrated. The virtual fab 400 includes a plurality of entities 402, 404, 406, 408, 410, 412, 414, 416 . . . , N that are connected by a communications network 418. The network 418 may be a single network or may be a variety of different networks, such as an intranet and the Internet, and may include both wireline and wireless communication channels.

In the present example, the entity 402 represents a service system for service collaboration and provision, the entity 404 represents a customer, the entity 406 represents an engineer, the entity 408 represents a metrology facility for IC testing and measurement, the entity 410 represents a fabrication (fab) facility, and the entity 412 represents a test facility, the entity 414 represents a defect pattern recognition system, and the entity 416 represents another virtual fab (e.g., a virtual fab belonging to a subsidiary or a business partner). Each entity may interact with other entities and may provide services to and/or receive services from the other entities.

For purposes of illustration, each entity 402-416 may be referred to as an internal entity (e.g., an engineer, customer service personnel, an automated system process, a design or fabrication facility, etc.) that forms a portion of the virtual fab 400 or may be referred to as an external entity (e.g., a customer) that interacts with the virtual fab 400. It is understood that the entities 402-416 may be concentrated at a single location or may be distributed, and that some entities may be incorporated into other entities. In addition, each entity 402-416 may be associated with system identification information that allows access to information within the system to be controlled based upon authority levels associated with each entities identification information.

The virtual fab 400 enables interaction among the entities 402-416 for the purpose of IC manufacturing, as well as the provision of services. In the present example, IC manufacturing includes receiving a customer's IC order and the associated operations needed to produce the ordered ICs and send them to the customer, such as the design, fabrication, testing, and shipping of the ICs.

One of the services provided by the virtual fab 400 may enable collaboration and information access in such areas as design, engineering, logistics, and defect control. For example, in the design area, the customer 404 may be given access to information and tools related to the design of their product via the service system 402. The tools may enable the customer 404 to perform yield enhancement analyses, view layout information, and obtain similar information. In the engineering area, the engineer 406 may collaborate with other engineers using fabrication information regarding pilot yield runs, risk analysis, quality, and reliability. The logistics area may provide the customer 404 with fabrication status, testing results, order handling, and shipping dates. In the defect control area, the engineer 406 may be given access to the defect pattern recognition system 414 and other sources such as the metrology facility 408, the fab facility 410, and the test facility via the network 418 to implement defect pattern processing. It is understood that these areas are exemplary, and that more or less information may be made available via the virtual fab 400 as desired.

Another service provided by the virtual fab 400 may integrate systems between facilities, such as between the metrology facility 408 and the fab facility 410. Such integration enables facilities to coordinate their activities. For example, integrating the metrology facility 408 and the fab facility 410 may enable manufacturing information to be incorporated more efficiently into the fabrication process, and may enable wafer data from the metrology tools to be returned to the fab facility 410 for improvement and incorporation.

Thus, the present disclosure provides a method of recognizing a defect image associated with a semiconductor substrate. In one embodiment, the method comprises: collecting defect data of the defect image by testing and measuring the semiconductor substrate; extracting a pattern from the defect data; normalizing the pattern of its location, orientation, and size; and identifying the pattern after the pattern is normalized.

In other embodiments, the defect image may comprise a particle distribution on the semiconductor substrate. The defect image may comprise a distribution of a parameter beyond a predefined failure criteria on the semiconductor substrate. The collecting defect data may comprise collecting data using a manufacturing system selected from the group consisting of a metrology facility, a fabrication facility, a test facility, and a combination. The extracting a pattern from the defect data may further comprise: filtering off lower density defects from the defect data, using a predefined criteria; and isolating the pattern from the defect data. The normalizing the pattern may comprise: relocating the pattern such that its density is centered; rotating the pattern such that a predefined line is oriented; and resizing the pattern such that pattern is unified to a predefined dimension. The predefined line comprises a line connecting two defect points most far away within the pattern. The resizing the pattern may comprise scaling the pattern such that the predefined line is scaled to the predefined dimension. The identifying the pattern may comprise: extracting parameters from the pattern after the normalizing the pattern; and matching the pattern to each of defect patterns in a database. The identifying the pattern may comprise: extracting parameters from the pattern after the normalizing the pattern; and analyzing the pattern using a predefined formula comprising the parameters extracted from the pattern.

The present disclosure further provides another embodiment of a method of recognizing a defect image associated with a substrate. The method comprises: collecting defect data of the defect image by testing and measuring the substrate; isolating a pattern from the defect data; normalizing the pattern; extracting parameters from the normalized pattern; and identifying the pattern using the normalized pattern and the extracted parameters. The normalizing the pattern further comprises relocating the pattern such that its density center is centered; rotating the pattern such that a predefined direction is oriented; and resizing the pattern to unified dimensions.

In the disclosed method, the substrate may be selected from the group consisting of a semiconductor wafer, a photomask, a liquid crystal display (LCD). The defect image may be selected from the group consisting of a particle distribution, a in-line failure distribution, and a test failure distribution. The collecting defect data may comprise collecting defect data by a manufacturing system selected from the group consisting of a metrology facility, a fabrication facility, a test facility, and a combination. The isolating a pattern may comprise filtering off lower density defect from the defect data, using a predefined criteria. The identifying the pattern may comprise analyzing the pattern using a predefined formula.

In still another embodiment, the present disclosure provides a system for recognizing a defect pattern on a semiconductor substrate. The system comprises an input module designed to collect defect data from a defect image formed on a semiconductor substrate; a pattern translation engine to normalize a pattern in location, orientation, and size, wherein the pattern is extracted isolated from the defect image; and a pattern recognition module designed to identify the pattern after the pattern is normalized by the pattern translation engine.

The disclosed system may further comprise a noise filter to eliminate lower density defects from the defect image. The disclosed system may further comprise a characteristic extraction module to extract parameters of the pattern for the pattern recognition module after the pattern is normalized. The disclosed system may further comprise an output module to present data from the pattern recognition module to users.

Although embodiments of the present disclosure have been described in detail, those skilled in the art should understand that they may make various changes, substitutions and alterations herein without departing from the spirit and scope of the present disclosure. Accordingly, all such changes, substitutions and alterations are intended to be included within the scope of the present disclosure as defined in the following claims. In the claims, means-plus-function clauses are intended to cover the structures described herein as performing the recited function and not only structural equivalents, but also equivalent structures.

What is claimed is:

1. A method for recognizing a defect image associated with a semiconductor substrate, comprising:
    collecting defect data of the defect image by testing and measuring the semiconductor substrate;
    extracting a defect pattern from the defect data;
    normalizing a location, orientation, and size of the defect pattern, wherein the normalizing includes determining a center of the defect pattern and shifting the defect pattern such that the center of the defect pattern is shifted from a first location of the semiconductor substrate to a second location of the semiconductor substrate;
    identifying the defect pattern after the normalizing by comparing the normalized defect pattern with standard defect patterns;
    performing a failure mode analysis based on the normalized defect pattern; and
    fabricating a semiconductor wafer based on the failure mode analysis.

2. The method of claim 1, wherein the defect image comprises a particle distribution on the semiconductor substrate.

3. The method of claim 1, wherein the defect image comprises a distribution of a parameter beyond a predefined failure criteria on the semiconductor substrate.

4. The method of claim 1, wherein the extracting the defect pattern from the defect data comprises:
    filtering off lower density defects from the defect data using at least one predefined criterion; and
    isolating the defect pattern from the defect data.

5. The method of claim 1, wherein the defect pattern includes a plurality of defects that each have a position, and wherein the determining the center of the defect pattern includes averaging the respective positions of all the defects in the defect pattern, and wherein the normalizing further includes:
- determining a predefined line connecting two defects separated by a distance within the defect pattern;
- rotating the defect pattern such that the predefined line is horizontally oriented; and
- resizing the defect pattern such that the defect pattern is adjusted in scale to a predefined dimension.

6. The method of claim 5, wherein the predefined line is defined as a line connecting two defects that are separated by a greatest distance within the defect pattern.

7. The method of claim 5, wherein the resizing the defect pattern includes scaling the defect pattern such that the predefined line is scaled to the predefined dimension.

8. The method of claim 1, wherein the identifying the defect pattern comprises:
- extracting parameters from the defect pattern after normalizing the defect pattern; and
- matching the normalized defect pattern to each of the standard defect patterns in a database.

9. The method of claim 1, wherein the identifying the defect pattern comprises:
- extracting parameters from the defect pattern after normalizing the defect pattern; and
- analyzing the defect pattern by using a predefined formula with the parameters extracted from the normalized defect pattern.

10. A method for recognizing a defect image associated with a substrate, comprising:
- collecting defect data of the defect image by testing and measuring the substrate using a metrology tool;
- isolating a pattern from the defect data;
- normalizing the pattern by a process including:
  - relocating the pattern such that its density center is relocated approximately at a center of the substrate;
  - rotating the pattern such that a predefined direction is oriented; and
  - resizing the pattern to unified dimensions;
- extracting parameters from the normalized pattern; and
- identifying the pattern using the normalized pattern and the extracted parameters;
- performing a failure mode analysis based on the normalized pattern and the extracted parameters; and
- fabricating a semiconductor wafer based on the failure mode analysis.

11. The method of claim 10, wherein the substrate is selected from the group consisting of a semiconductor wafer, a photomask, and a liquid crystal display (LCD).

12. The method of claim 10, wherein the defect image is selected from the group consisting of a particle distribution, a in-line failure distribution, and a test failure distribution.

13. The method of claim 10, wherein collecting the defect data comprises collecting defect data by a manufacturing system selected from the group consisting of a metrology facility, a fabrication facility, a test facility, and a combination.

14. The method of claim 10, wherein isolating a pattern comprises filtering off lower density defects from the defect data using a predefined criterion.

15. The method of claim 10, wherein identifying the pattern comprises analyzing the pattern using a predefined formula.

16. A system for recognizing a defect pattern on a semiconductor substrate, comprising:
- an input module designed to collect defect data from a defect image formed on a semiconductor substrate;
- a pattern translation engine to normalize a defect pattern in location, orientation, and size, wherein the defect pattern is extracted from the defect image and includes a plurality of defects, and wherein the normalization of the defect pattern includes determining a center of the defect pattern and relocating the defect pattern such that the center is relocated from a first location of the substrate to a second location of the substrate; and
- a pattern recognition module designed to identify the defect pattern after the defect pattern is normalized by the pattern translation engine.

17. The system of claim 16 further comprising a noise filter to eliminate lower density defects from the defect image.

18. The system of claim 16 further comprising a characteristic extraction module to extract parameters of the defect pattern for the pattern recognition module after the defect pattern is normalized.

19. The system of claim 16 further comprising an output module to present data from the pattern recognition module to users.

20. The system of claim 17 wherein the normalization of the defect pattern further includes:
- determining a predefined line connecting two defects separated by a greatest distance within the defect pattern;
- rotating the defect pattern such that the predefined line is horizontally oriented; and
- resizing the defect pattern so that that the defect pattern fits within a predefined area.

* * * * *